United States Patent [19]

Annis

[11] Patent Number: 4,573,983
[45] Date of Patent: Mar. 4, 1986

[54] LIQUID COLLECTION SYSTEM HAVING AN ANTI-SEPTIC MEMBER ON THE DISCHARGE SECTION

[75] Inventor: Larry D. Annis, Elgin, Ill.
[73] Assignee: The Kendall Company, Boston, Mass.
[21] Appl. No.: 635,017
[22] Filed: Jul. 27, 1984
[51] Int. Cl.$^4$ .............................................. A61M 1/00
[52] U.S. Cl. ................. 604/322; 210/205; 128/760; 128/762; 128/767
[58] Field of Search ............... 128/204.13, 203.23, 128/762, 760, 766, 767, 771, DIG. 24; 210/753, 764, 205; 604/317, 322–326

[56] References Cited

U.S. PATENT DOCUMENTS

| | | | |
|---|---|---|---|
| 4,333,480 | 6/1982 | Villari et al. | 128/767 |
| 4,372,313 | 2/1983 | Villari et al. | 128/295 |
| 4,417,892 | 11/1983 | Meisch | 604/323 |
| 4,460,362 | 7/1984 | Bates | 604/323 |
| 4,464,258 | 8/1984 | Wong et al. | 210/205 |

FOREIGN PATENT DOCUMENTS 7230508  8/1972  Japan .................... 210/764

*Primary Examiner*—J. L. Kruter
*Attorney, Agent, or Firm*—Powell L. Sprunger

[57] ABSTRACT

A liquid collection system comprising, a drainage container having a chamber for collection of liquid therein, and a flexible tubular section communicating with a lower portion of the chamber. The system has a clamp on the tubular section for releasably closing the tubular section. The system also has an antiseptic device secured to an outer end of the tubular section, with the device having an annular wall defining a cavity, at least one well for capturing liquid adjacent an outer end of the cavity, and a pocket for capturing liquid adjacent an inner end of the cavity. The device has a capsule in the cavity containing an antiseptic agent.

6 Claims, 4 Drawing Figures

LIQUID COLLECTION SYSTEM HAVING AN ANTI-SEPTIC MEMBER ON THE DISCHARGE SECTION

BACKGROUND OF THE INVENTION

The present invention relates to liquid collection systems.

Liquid drainage systems of the type for draining urine from the bladder of a patient are known. Such systems generally comprise a catheter having a distal end received in the bladder, and a drainage tube connected to a proximal end of the catheter outside the patient's body. A collection bag is connected to a downstream end of the drainage tube, and urine drains from the bladder through the catheter and drainage tube into the bag for retention therein.

Such systems are sterile and are closed to the atmosphere to prevent the introduction of bacteria into the system with possible harmful results to the patient. The bags of such systems are normally provided with a lower tubular section and a clamp on the tubular section which may be opened to periodically drain urine from the bag. However, the tubular section may permit the passage of bacteria through the tubular section into the bag resulting in contamination to the system.

SUMMARY OF THE INVENTION

A principal feature of the present invention is the provision of an improved liquid collection system.

The liquid collection system of the present invention comprises, a drainage container having a chamber for collection of liquid therein, a flexible tubular section communicating with a lower portion of the chamber, and a clamp on the tubular section for releasably closing the tubular section. The system has an antiseptic device secured to an outer end of the tubular section, with the device having an annular wall defining a cavity, at least one well adjacent an outer end of the cavity, and a pocket adjacent an inner end of the cavity. The device has a capsule in the cavity containing an antiseptic agent.

A feature of the present invention is that when the clamp is opened and urine drains from the bag through the tubular section, urine is captured in the wells.

Another feature of the invention is that when urine has been drained from the container and after the clamp has been closed, the tubular section is lifted, and urine drains from the wells into the pocket for retention wherein after having been treated by the antiseptic agent to kill bacteria therein.

A further feature of the invention is that some of the urine will also drain back to the closed clamp.

Yet another feature of the invention is that the treated urine in the pocket and adjacent the closed clamp contains antiseptic agent from the capsule and prevents the retrograde movement of bacteria through the device and tubular section.

Thus, a feature of the present invention is that the device prevents the introduction of bacteria into the bag.

Further features will become more fully apparent in the following description of the embodiments of this invention and from the appended claims.

DESCRIPTION OF THE PREFERRED EMBODIMENTS

Figure 1:
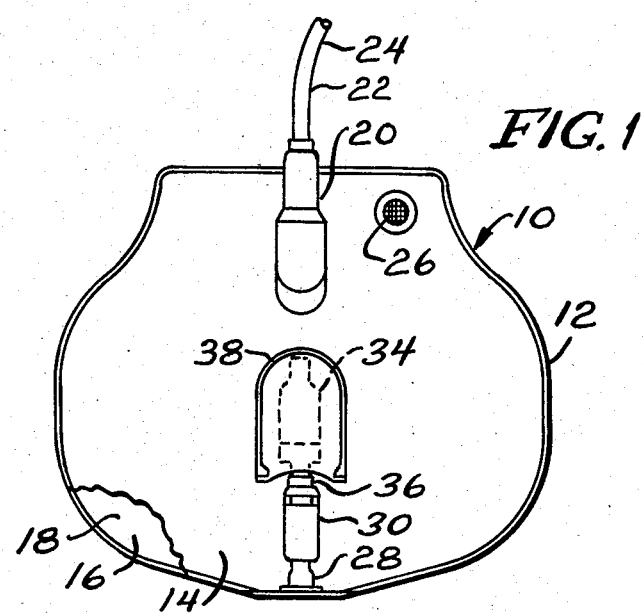
FIG. 1 is a fragmentary elevational view, partly broken away, of a liquid collection system of the present invention with a tubular section at a lower portion of a drainage container being placed in an upright position.

Referring now to FIG. 1, there is shown a liquid collection system generally designated 10 comprising a collection bag 12. The bag 12 has a front wall 14 of flexible material, and a back wall 16 of flexible material, such as a suitable plastic, with the front wall 14 and back wall 16 being joined at their periphery in order to define a chamber 18 between the walls 14 and 16. The bag has a connector 20 secured to an upper portion of the front wall 14, such that the connector 20 communicates with the chamber 18. A downstream end 22 of a drainage tube 24 is secured to the connector 20, such that the drainage tube 24 communicates through the connector 20 with the chamber 18. The bag 12 may have a filter 26 of air pervious, bacteria impervious material, such as known to the art, to permit passage of air from the atmosphere into the chamber 18 while preventing the passage of bacteria from the atmosphere into the chamber 18.

In use of the bag 12, a distal end of a catheter (not shown) is passed through the urethra of a patient until the distal end of the catheter is located in the patient's bladder, and a proximal end of the catheter located outside the patient's body is connected to an upstream end of the drainage tube 24. During catheterization, urine passes from the bladder through the catheter and drainage tube 24 into the bag chamber 18 for retention therein. As urine collects and fills the chamber 18, it is necessary to periodically empty the urine from the chamber 18.

Figure 2:
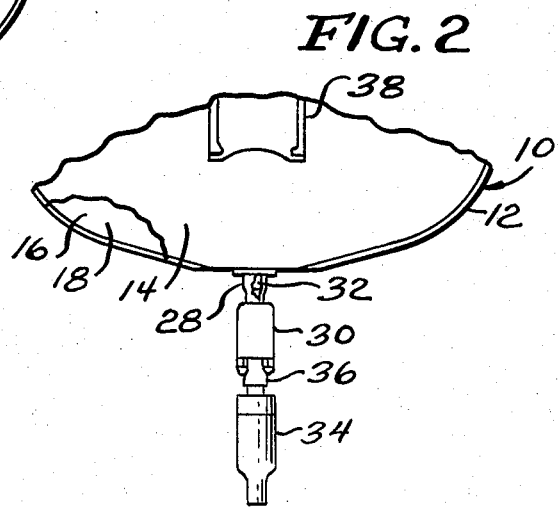
FIG. 2 is a fragmentary elevational view of the collection system of FIG. 1 with the tubular section in a lower position.

For this purpose, the bag 12 has a flexible or elastic tubular section 28 secured to a lower portion of the bag 12 and communicating with a lower portion of the chamber 18. The tubular section 28 has a suitable clamp 30 of a type known to the art secured on the tubular section 28 in order to open and close a lumen 32 in the tubular section 28. The system 10 has an antiseptic device 34 secured to an outer end 36 of the tubular section 28. During collection of urine in the chamber 18, the tubular section 28 and antiseptic device 34 are placed in an upright position, as shown in FIG. 1, with the antiseptic device 34 received in a pocket 38 on the front wall 14. Thus, the tubular section 28 and antiseptic device 34 are located in a normal storage position with the clamp 30 closed. However, when it is desired to empty urine from the bag chamber 18, the antiseptic device 34 is removed from the pocket 38, as shown in FIG. 2, such that the tubular section 28 and antiseptic device 34 depend from a lower end of the collection bag 12. Next, the clamp 30 is opened in order to permit passage of urine through the tubular section 28 and through the antiseptic device 34 which will be further described below. In this manner, the bag chamber 18 is emptied through the tubular section 28 and antiseptic device 34.

Figure 3:
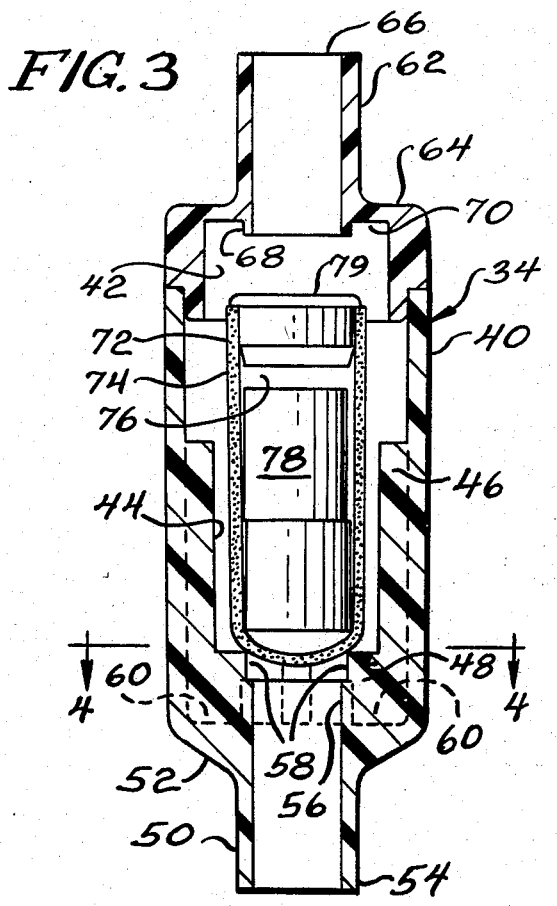
FIG. 3 is a fragmentary sectional view of an antiseptic device attached to the tubular section of FIGS. 1 and 2.
Figure 4:
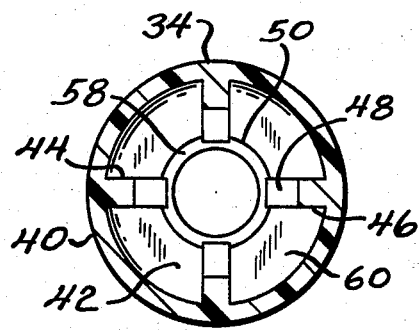
FIG. 4 is a sectional view taken substantially as indicated along the line 4—4 of FIG. 3.

With reference to FIGS. 3 and 4, the antiseptic device 34 has an annular wall 40 defining a cavity 42 inside the wall 40. The device 34 has a plurality of inwardly directed ribs 44 in the cavity 42 with side portions 46 and inwardly directed base portions 48. The antiseptic device 34 has a tubular section 50 at an outer end of the cavity 42, with an outer portion 54 being located outside the cavity 42, and an inner portion 56 being located inside the cavity 42. As shown, the inner portion 56 of the tubular section 50 is spaced below the base portions 48 in order to define openings 58 between the base portions 48. Also, the base portions 48 and tubular section 50 define a plurality of wells 60 adjacent the outer end 52 of the cavity 42 for a purpose which will be described below.

The device 34 has a second tubular section 62 adjacent an inner end 64 of the cavity 42. The tubular section 62 has an inner portion 66 located outside the cavity 42, and an outer portion 68 projecting into the cavity 42, such that the outer portion 68 of the tubular section 62 and the wall 40 define a pocket 70 extending circumferentially around the cavity 42.

The device 34 has a capsule 72 received in the cavity 42, with the capsule 72 having an annular liquid pervious wall 74 defining a cavity 76 to receive a suitable antiseptic agent, such as pellets 78 constructed from a suitable antiseptic material, such as povidone iodine. The capsule 72 also has a cap 79 which releasably closes an end of the cavity 76 in order to retain the pellets 78 in the cavity 76. The wall 74 of the capsule 72 is constructed from a liquid pervious material in order to permit passage of urine through the wall 74 into contact with the pellets 78 in order to kill bacteria in the urine.

In use of the system 10, after the tubular section 28 and antiseptic device 34 have been moved to the lower position, as shown in FIG. 2, and the clamp 30 is opened, urine passes through the tubular section 28 and into the cavity 42 after which it saturates the wall 74 of the capsule 72 and comes in contact with the antiseptic pellets 78. The treated urine further passes from the capsule 72 to the outer end 52 of the cavity 42, and a major portion of the treated urine passes through the tubular section 50 for disposal, while a minor portion of the treated urine is captured in the wells 60. After all the urine has been drained from the bag chamber 18, the clamp 30 is closed, and the tubular section 28 and antiseptic device 34 are moved to the storage position as shown in FIG. 1. During this time, the treated urine trapped in the wells 60 passes along the capsule 72 toward the inner end 64 of the cavity 42. Part of the treated urine is then captured in the pocket 70, while a part of the treated urine passes through the second tubular section 62 to the closed clamp 30 where it is stopped. Thus, in the storage position of FIG. 1, the treated urine in the pocket 70 provides a barrier against the passage of urine through the antiseptic device 34, and bacteria will be killed by the treated urine in the pocket 70. In the unlikely event that some of the bacteria may pass the pocket 70, the bacteria will be killed by the remaining portion of treated urine retained above the closed clamp 30. Thus, a liquid collection system 10 is disclosed in which treated urine is trapped during storage of a tubular section 28 and the antiseptic device 34 in order to prevent passage of bacteria through the antiseptic device 34 and tubular section 28 into the collection bag 12.

The foregoing detailed description is given for clearness of understanding only, and no unnecessary limitations should be understood therefrom, as modifications will be obvious to those skilled in the art.

I claim:

1. A urine drainage collection system, comprising:
a drainage container having a chamber for collection of liquid therein;
a flexible tubular discharge section having an outer end in fluid communication with a lower portion of said chamber for discharge of collected urine;
a clamp on said tubular section for releasably opening and closing the tubular section; and
a tubular anti-septic device means containing an antiseptic capsule in fluid communication with the outer end of the tubular discharge section, said device having an annular wall and inner and outer sections forming a cavity to contain said antiseptic capsule, base portion means at the outer end of said tubular device means forming at least one well portion, said well portion acting to trap minor portions of urine when urine is discharged from said container chamber, a pocket means formed by projections at the inner section of the tubular device to act as a barrier trap against the passage of urine back to the collection bag when the antiseptic device and the flexible tubular discharge section are inverted from a discharge condition to a storage condition.

2. The system of claim 1 wherein the device has a plurality of wells adjacent the outer end of the cavity.

3. The system of claim 1 wherein the device has a plurality of inwardly directed ribs in the cavity.

4. The system of claim 1 wherein the device has a plurality of openings above the wells intermediate the ribs.

5. The system of claim 1 wherein the pocket extends circumferentially around the cavity.

6. The system of claim 1 wherein the capsule has a liquid pervious wall, and in which the antiseptic agent is retained inside the wall.

* * * * *